(12) United States Patent
Grebius

(10) Patent No.: US 8,845,647 B2
(45) Date of Patent: Sep. 30, 2014

(54) DEVICE FOR MIXING AND APPLYING A PASTE, SUCH AS BONE CEMENT

(75) Inventor: Staffan Grebius, Lund (SE)

(73) Assignee: Proxima Medical AB, Lund (SE)

( * ) Notice: Subject to any disclaimer, the term of this patent is extended or adjusted under 35 U.S.C. 154(b) by 583 days.

(21) Appl. No.: 13/002,296

(22) PCT Filed: Jun. 30, 2009

(86) PCT No.: PCT/SE2009/050842
§ 371 (c)(1),
(2), (4) Date: May 2, 2011

(87) PCT Pub. No.: WO2010/002346
PCT Pub. Date: Jan. 7, 2010

(65) Prior Publication Data
US 2011/0270260 A1    Nov. 3, 2011

Related U.S. Application Data

(60) Provisional application No. 61/077,357, filed on Jul. 1, 2008.

(30) Foreign Application Priority Data

Jul. 1, 2008   (SE) ...................................... 0801563

(51) Int. Cl.
*A61B 17/58*   (2006.01)
*A61B 17/60*   (2006.01)
*A61F 2/00*    (2006.01)
*B01F 11/00*   (2006.01)
*B01F 13/00*   (2006.01)
*B01F 15/02*   (2006.01)
*B01F 15/00*   (2006.01)
*A61B 17/88*   (2006.01)

(52) U.S. Cl.
CPC ....... *B01F 11/0054* (2013.01); *B01F 15/00506* (2013.01); *B01F 13/0023* (2013.01); *A61B 2017/8838* (2013.01); *B01F 15/0279* (2013.01); *A61B 17/8825* (2013.01); *B01F 13/002* (2013.01)
USPC .................................. 606/94; 606/92; 606/93

(58) Field of Classification Search
USPC ...................................................... 606/92–94
See application file for complete search history.

(56) References Cited

U.S. PATENT DOCUMENTS

| 5,306,248 A * | 4/1994 | Barrington ................. 604/97.02 |
| 6,406,175 B1 | 6/2002 | Marino |
| 6,595,946 B1 * | 7/2003 | Pasqualucci .................... 604/27 |
| 2005/0105385 A1 * | 5/2005 | McGill et al. ................. 366/139 |

FOREIGN PATENT DOCUMENTS

WO   WO 2004/002615 A1   1/2004

OTHER PUBLICATIONS

International Search Report for corresponding International Application PCT/SE2009/050842.
* cited by examiner

*Primary Examiner* — Andrew Yang
*Assistant Examiner* — Olivia C Chang
(74) *Attorney, Agent, or Firm* — Merchant & Gould P.C.

(57) ABSTRACT

A device for mixing, dispensing and applying a paste, such as bone cement, has a housing (1), a cylinder (4) for receiving the paste, and a piston (13) associated with a piston rod (7). A mixing paddle (12) is provided with ridges (23) for engagement with grooves (24) on the piston (13). By this engagement, the paddle-piston assembly (12-13) can be rotated after removal of a safety pin (9) and interconnected by a jamming mechanism (25). After this interconnection, the paddle-piston assembly (12-13) is used to push the paste inside the cylinder (4) and out thereof for dispensing. A low-friction piston rod locking mechanism (14) is provides as well.

10 Claims, 6 Drawing Sheets

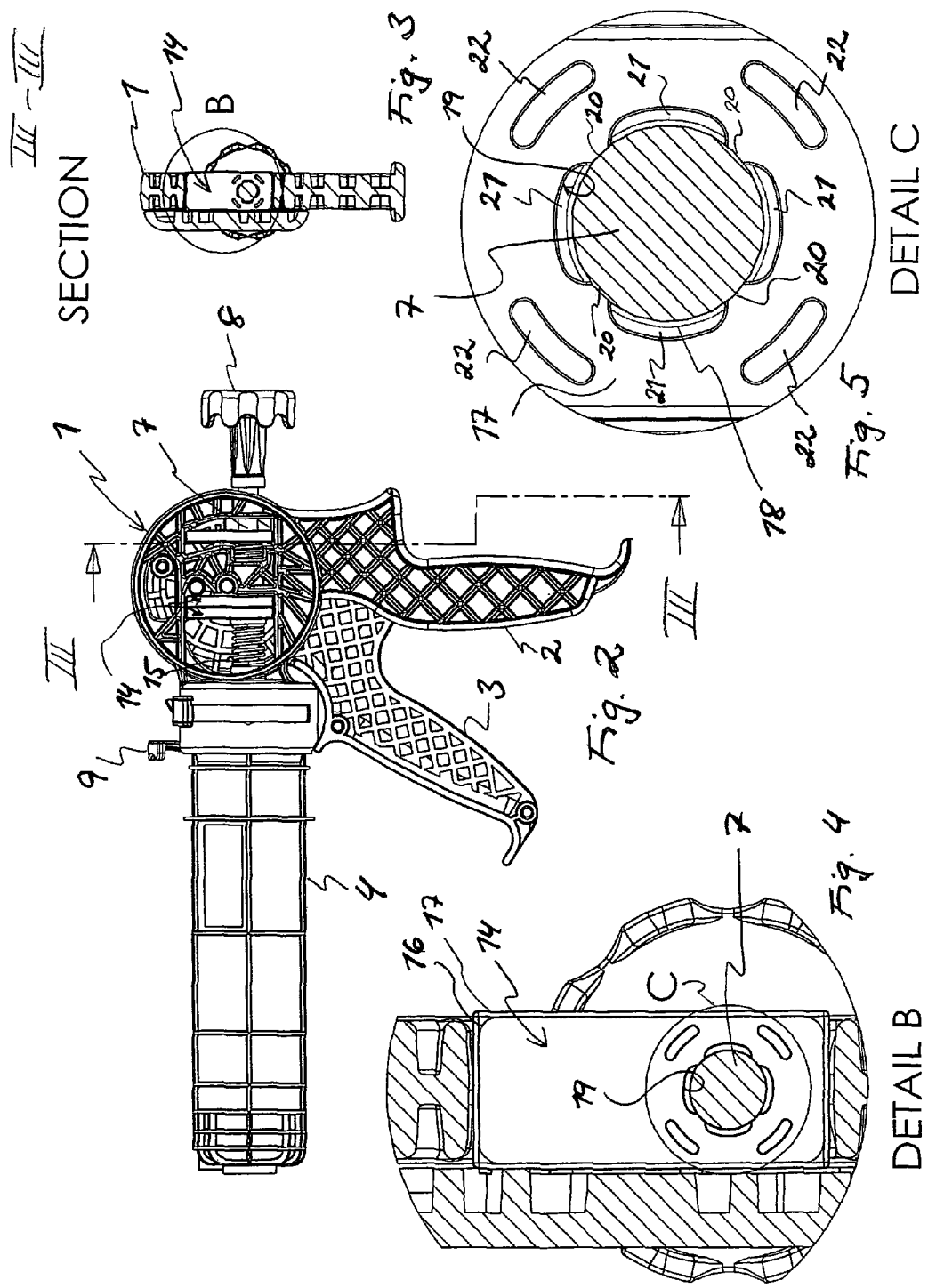

DEVICE FOR MIXING AND APPLYING A PASTE, SUCH AS BONE CEMENT

CROSS-REFERENCE TO RELATED APPLICATIONS

This application is a National Stage Application of PCT/SE2009/050842, filed on Jun. 30, 2009, which claims the benefit of Serial No. 0801563-8, filed Jul. 1, 2008 in Sweden, and which also claims benefit of Ser. No. 61/077,357, filed Jul. 1, 2008 in the USA and which applications are incorporated herein by reference. To the extent appropriate, a claim of priority is made to each of the above disclosed applications.

TECHNICAL FIELD

The present invention relates to a device for mixing paste ingredients and delivering pastes that require mixing prior to delivering, and more particularly to a single-use device which is able to handle such pastes as bone cement.

BACKGROUND

In general terms, bone cement is used for instance in connection with surgery like replacement of hip joints and spinal disc enhancements. The bone cement is a powder-like material which before use is mixed with a liquid (monomere) to form a paste. Normally, the bone cement contains acrylate plastic which is biocompatible, whereas the liquid contains an ester. For hip joint replacements, the viscosity of the bone cement paste is often quite high, whereas the bone cement paste used for spinal disc enhancements has lower viscosity.

For simplicity, the term bone cement will be used throughout this application, although the invention can be used for other kinds of paste which is used for similar surgery and which requires mixing prior to application.

An example of a prior-art device of this kind is disclosed in WO-A-04/002615 the contents of which are included herein by reference. This known device is used for mixing, dispensing and applying paste and it has been tested in practice with good results. However, there is still room for improvements.

The device of WO-A-04/002615 has a housing-cylinder assembly with a piston rod arranged displaceable and rotatable therein. At its free end within the cylinder, the piston rod is provided with mixing means and the piston rod is interconnected to a piston which is displaceable within the cylinder. In a mixing mode, the piston is kept stationary whereas the mixing means is displaced and rotated within the cylinder, by means of the rod, for mixing the bone cement and the liquid contained in the cylinder to form the aimed-at paste. In a dispensing mode, the mixing means and the piston are connected to each other to form a unit which is displaced axially within the cylinder and thereby pushes the mixed paste out of an dispensing opening at the free end of the cylinder.

In order to bring the device into dispensing mode, the operator handling the device has to turn an external ring which interconnects the piston and the piston rod so that the mixed paste can be pressed out of the cylinder. This is a somewhat difficult operation since the operator has to turn the external ring at the same time as he holds and pushes the external knob of the piston rod. Since the external ring is turnable only in one direction for connecting purposes, left-handed surgeons may find the device hard to handle in this mode.

A general requirement of devices like this, is that the displacement of the piston rod is smooth and easy to accomplish. However, the metal-against-metal contact between the piston rod and the locking members within the housing may cause scratches on the surface of the piston rod which in turn can create a risk of undesired metal fragments or particles. The scratches may also create a risk for tiny ruptures on sealing rings within the device which may lead to air leakage which in severe cases can result in undesired air cavities in the bone cement paste.

SUMMARY

An object of the present invention is to provide a paste mixing and applying device which is improved over the prior-art discussed above. In particular, the invention aims at facilitating the handling of the device.

These objects have been achieved by a device having the features set forth in the appended independent claims, preferred embodiments being defined in the dependent claims.

In one aspect of the invention, the mixing element of the piston rod has coupling means for engagement with matching coupling means on the piston. Owing to these co-operating coupling means, the piston and the piston rod can easily be interconnected and ready for the dispensing mode. The operator does not have to turn any external ring, but only has to handle the piston rod for achieving the desired interconnection. Furthermore, since no components are in metal-against-metal contact the risk of undesired metal particles is eliminated.

In a preferred embodiment, the mixing element is disposed at the end of the piston rod and its coupling means comprise projections directed to the piston whereas the piston coupling means comprise matching recesses configured to receive the projections. This embodiment is favourable since a secure rotational movement can be achieved. Preferably, the projections are elongate ridges and grooves disposed about the piston rod in the piston.

In another aspect of the invention, a locking member for locking the piston rod comprises an elastic material having an aperture the inner edge of which is at least partially in contact with the piston rod. The elastic material is configured to prevent contact between the piston rod and the inner edge of the locking member aperture. Thanks to this structure, the friction between the piston rod is reduced which enhances the displacement of the same at the same time as the risk of undesired surface scratches and metal particles is eliminated. A kind of "floating piston rod" is achieved.

In a preferred embodiment, the locking member comprises a plate-shaped element and the elastic material comprises a cover element having an aperture coaxial with the aperture of the plate element and at least one projection in contact with the piston rod. The contact between elastic material projection and the piston rod leads to a low-friction movement without metal-metal contact. Preferably, the cover element comprises a number of angularly spaced and opposed projections in contact with the piston rod. By this embodiment, a secure low-friction movement of the piston rod is achieved.

In a further embodiment, there is a pair of similar locking members covered by the elastic material and configured to prevent contact between the piston rod and the inner edge of the locking member aperture. By these dual locking members, a secure locking effect is achieved as well as a low-friction effect with respect to the movement of the piston rod.

Preferably, the plate element constituting the locking member is of metal whereas the elastic material is plastics, whereby a low friction effect and secure locking is accomplished.

In still another embodiment, the device comprises a releasable latching member which in the mixing mode prevents both rotation and displacement of the piston, and which in the dispensing mode is removed for allowing rotation and displacement of the piston-mixing member assembly within the cylinder. By this structure, the prior-art external ring can be avoided and a distinct handling of the device is achieved.

BRIEF DESCRIPTION OF THE DRAWINGS

In the following, the present invention will be described in more detail, reference being had to the accompanying schematic drawings which illustrate non-limiting embodiments and examples related to the invention.

FIG. 2 is a cross sectional view of the device shown in FIG. 1.

FIG. 3 is a sectional view along the line III-III in FIG. 2.

FIG. 4 shows a detail B of FIG. 3 on a larger scale.

FIG. 5 shows a detail C of FIG. 4 on a larger scale.

DETAILED DESCRIPTION OF EMBODIMENTS

Figure 1:
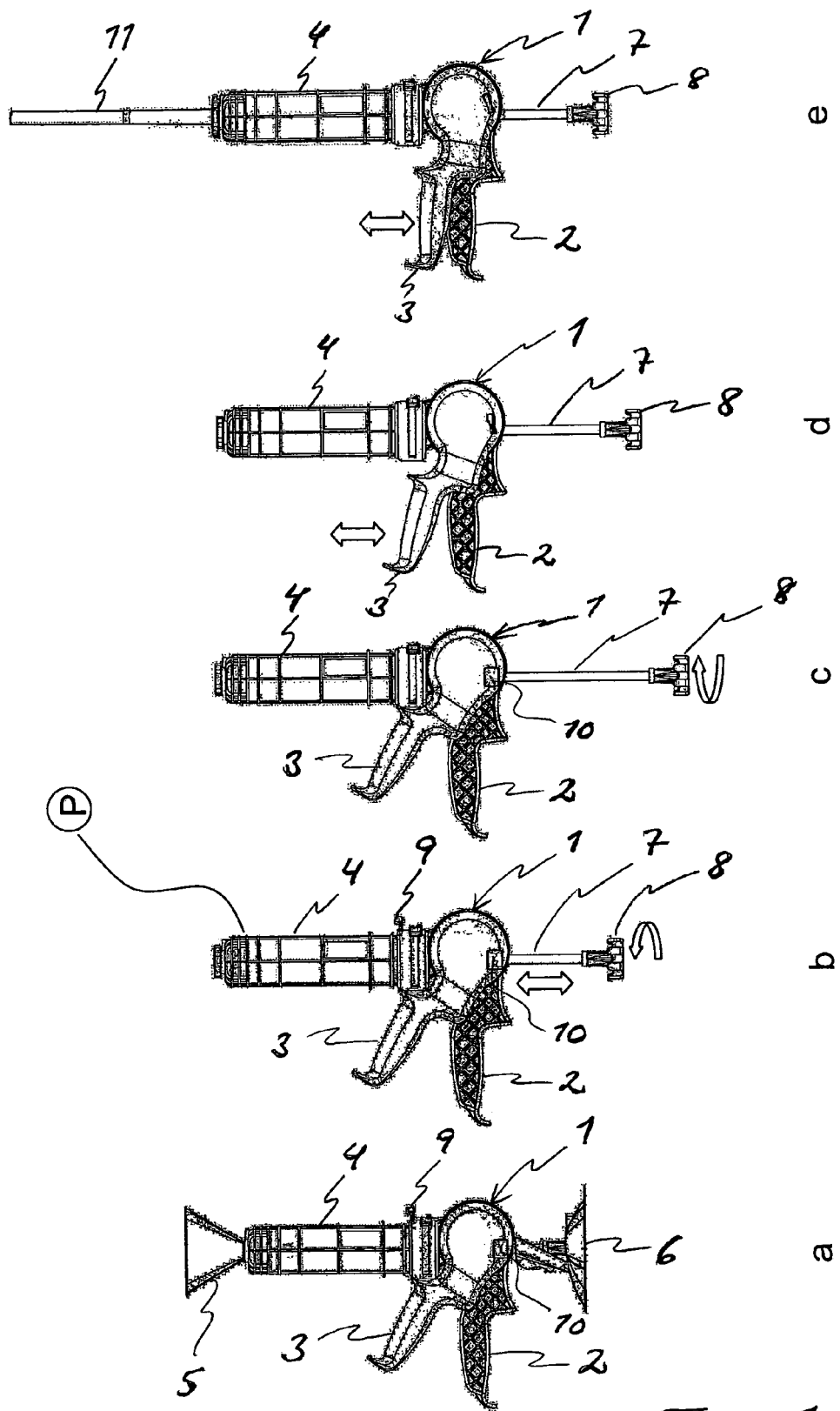
FIGS. 1a-1e are side views of a device according to an embodiment of the invention, in different operation modes.

A device according to an embodiment of the present invention is illustrated in FIGS. 1a-1e which show a sequence of steps performed before the device is to be used. The main components of the device are: a housing 1, a stationary handle part 2, a trigger handle part 3 and a cylinder 4.

As will be further described below, a paste of bone cement and liquid is mixed in the cylinder 4 and dispensed out of the same and applied in an surgical operation, such as a hip replacement. The bone cement powder and the liquid (monomer) are fed into the cylinder 4 through a funnel 5. During this filling, the device shown in FIG. 1a is placed vertically on a base member 6 and with the funnel 5 upwards.

In a mixing step shown in FIG. 1b, the funnel 5 and the base member 6 are removed and the cylinder 4 is closed at its free end. By means of a piston rod 7 and a knob 8, mixing means (to be described later) are moved within the cylinder 4 in order to mix the paste ingredients (bone cement and liquid) into the aimed-at paste. In this step, the piston rod 7 is axially displaced (pushed and pulled) several times within the cylinder 4 by means of the knob 8 as is shown by a double arrow. Furthermore, the piston rod 7 may be rotated by the knob 8 which is held by the operator (see arrow). In this step, a vacuum source P is connected to the cylinder 4 which reduces the presence of gas in the paste to be mixed. A latching member or safety pin 9 holds the piston stationary in the cylinder 4 by means of a ring.

In the step shown in FIG. 1c, the safety pin 9 is removed and the end of the piston rod 7 disposed in the cylinder 4 is connected to the piston within the cylinder 4 in a manner to be described. Thereafter, the piston and the piston rod 7 are interconnected and moveable together. The device is now ready for dispensing.

In FIG. 1d, a locking pin 10 shown in FIG. 1c has been removed which makes it possible to move the piston within the cylinder 4 containing the mixed paste. By moving the trigger handle part 3 back and forth (see double arrow), the piston is pressed against the paste. In a final step before use shown in FIG. 1e, a dispensing tube or nozzle 11 is connected to the free end of the cylinder 4 and further reciprocing movements of the trigger handle part 3 will press the paste out of the cylinder 4 and the nozzle tube 11 to the operation area, for instance the hip joint area of a patient.

Figure 6:
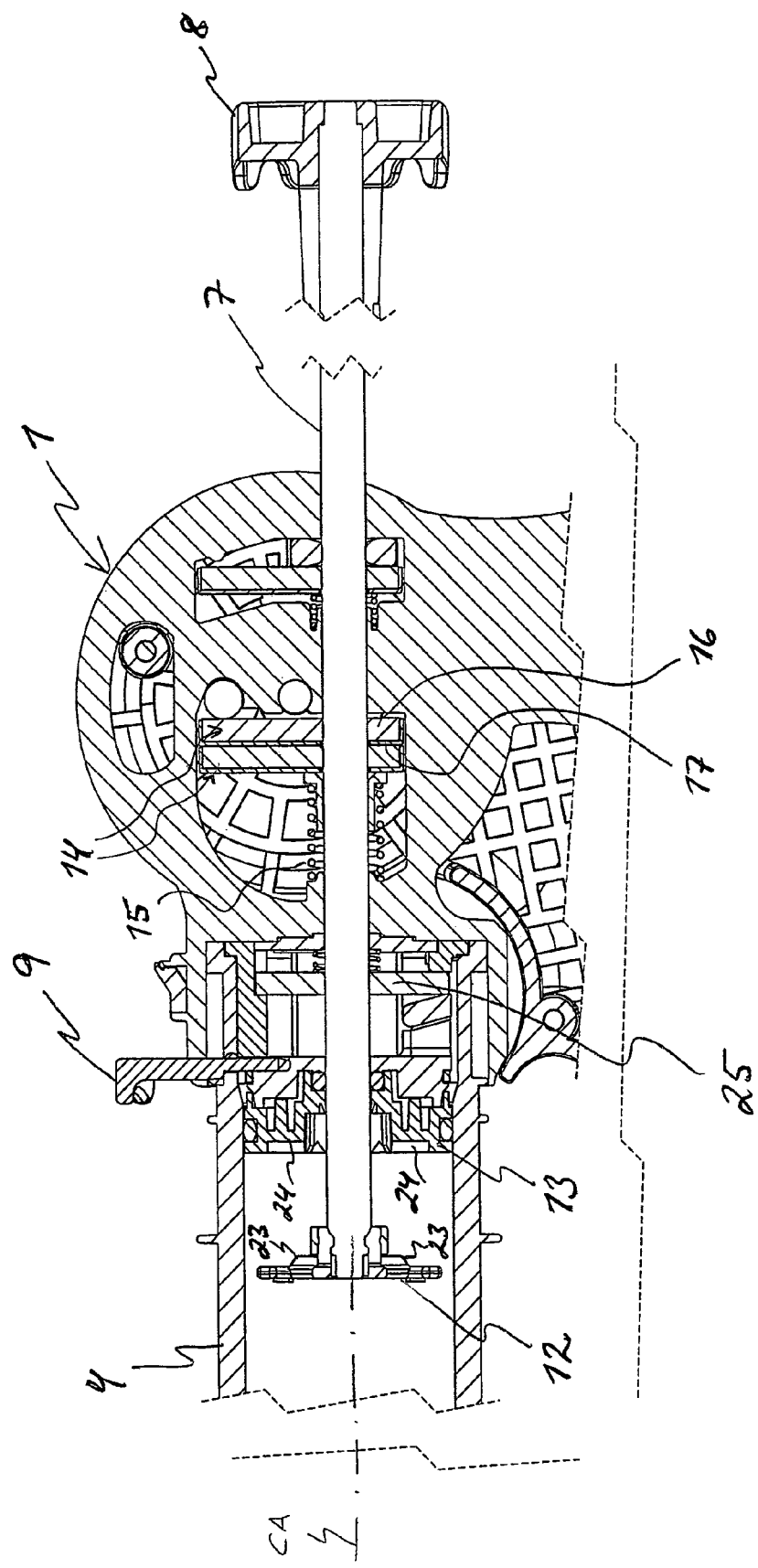
FIG. 6 shows a fragmentary section of the device of FIG. 2 on a larger scale, the device being in a mixing mode.

With reference to FIGS. 2-6, it is shown how the piston rod 7 is arranged in the housing 1. For illustrative purposes, the piston rod 7 is not shown with sectional lines. At its end within the cylinder 4 the piston rod 7 has a mixing means 12 also referred to as "a paddle" by persons skilled in the art. Also contained in the cylinder 4 is the piston 13 (see FIG. 6) earlier discussed with respect to FIG. 1. The piston rod 7 is displaceable in the piston 13 through a bore in the same. In FIG. 6, it is also shown how the safety pin 9 holds the piston 13.

A locking and feeding mechanism—according to one aspect of the invention—is contained in the housing 1 and includes two identical locking members 14 disposed in a cavity. The locking members 14 are biased by a spring 15 mounted in this cavity. In operation, the locking members 14 serve to lock the piston rod 7 to the piston 13 by jamming in any position along the length of the piston rod 7.

Each locking member 14 consists of a rectangular plate-shaped element 16 of metal and a matching rectangular cover element 17 of elastic material, preferably plastics. The plate element 16 has an aperture 18 for receiving the piston rod 7 (see FIG. 5). Hence, the inner diameter of this aperture 18 is somewhat larger than the diameter of the piston rod 7.

The plastic cover element 17 has an aperture 19 with an inner edge portion of a specific design for reducing the friction between the locking member 14 and the piston rod 7. The cover element aperture 19 has four projections 20 which are in contact with the outside of the piston rod 7 and which are equidistantly spaced along the perimeter of the aperture 19. Between the projections 20 there are cut-outs 21 extending along the perimeter of the aperture 19. By this structure, the only contact points between the piston rod 7 and the locking member 14 are the four elastic projections 20 of the cover element 17.

From FIG. 5 it can be seen that the "diameter" of the cover element 17 aperture 19 is somewhat larger than the diameter of the piston rod 5. Further, it is shown that the two apertures 18 and 19 are coaxial with respect to each other and the centre axis CA of the piston rod 7.

The elastic cover element 17 has four additional cuts 22 which enhance the elastic properties of the cover element 17.

By this structure, a "floating rod feature" is achieved, that is very low friction between the locking members 14 and the piston rod 7. Furthermore, thanks to the avoidance of metal-against-metal contact the risk of metal particles is eliminated.

Figure 9:
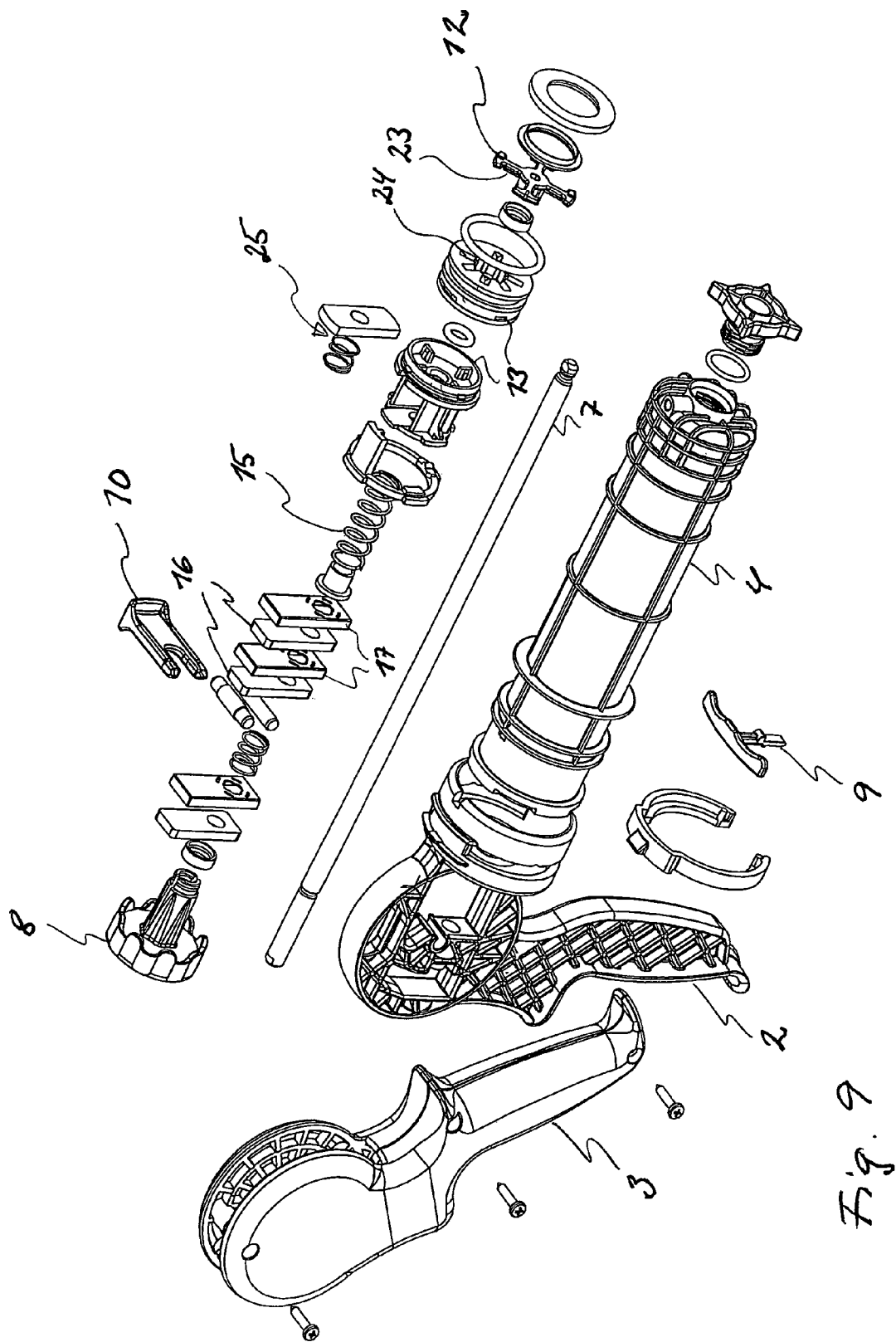
FIG. 9 is an exploded view of the device of FIG. 2.

The design of the locking members 14 are also understood from the exploded view in FIG. 9. Each plastic cover element 17 is basically a "box" with a base portion surrounded by four side portions. The "box" defines a rectangular recess in which a plate-shaped element 16 is placed. Thus, when mounted in the device each locking member 14 has one side covered by plastic material and its peripheral edge portions also covered by plastic material. One side is not covered, but exposes the metal.

Figure 7:
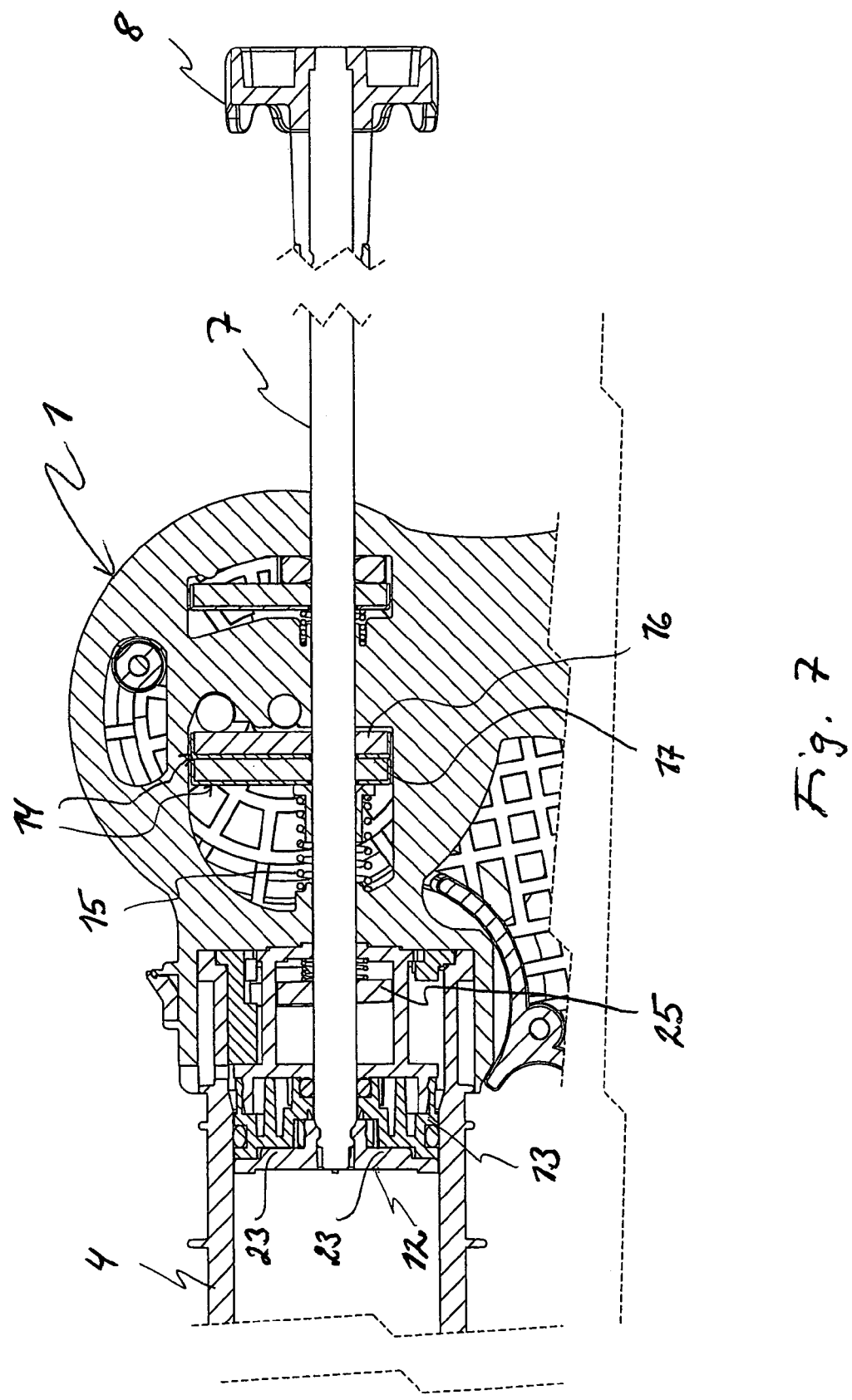
FIG. 7 shows the device of FIG. 6 in an inter-connecting mode.
Figure 8:
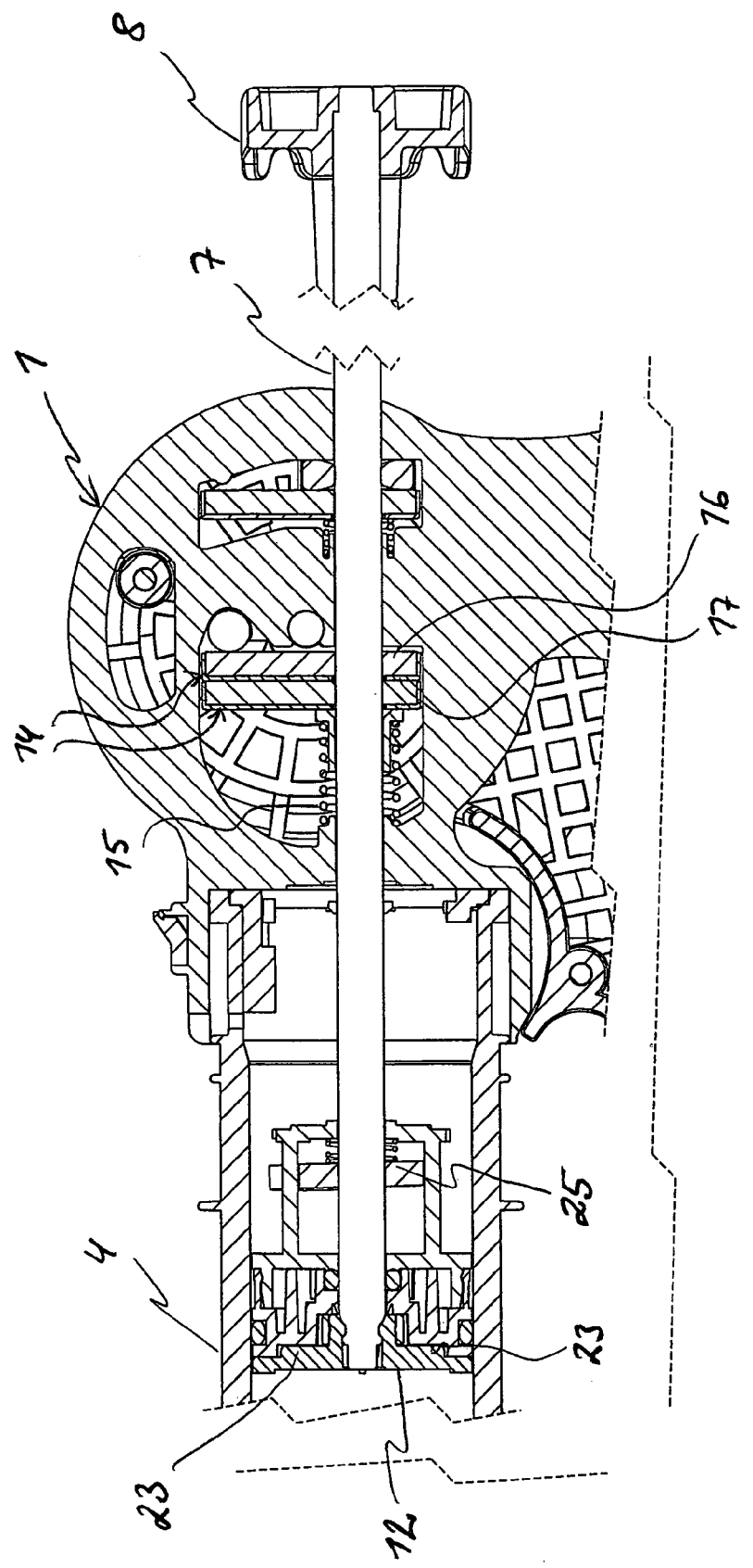
FIG. 8 shows the device of FIGS. 6-7 in a dispensing mode.

As can be seen in FIGS. 6-8, further locking members of the same type can be arranged in cavities in the housing.

In FIGS. 6-8 another aspect of the invention is presented as well. In the mixing mode of FIG. 6, the mixing paddle 12 is disconnected from the piston 13 which is held stationary by the safety pin 9. When the mixing procedure is terminated, the paddle 12 is to be connected to the piston 13 so that these two members can be pushed by the piston rod 7 as a unit. In prior-art devices, this interconnection is achieved by an external ring which is difficult to handle and which may create a risk of undesired metal particles inside the housing due to metal components moved by the external ring. By an inventive improvement, these drawbacks have now been set back.

According to this embodiment (see FIG. 6), the paddle 12 has coupling means in the shape of elongate ridges 23 which are directed to the piston 13 and which are configured to match corresponding coupling means in the shape of elongate grooves 24 formed in the piston 13 and directed to the paddle 12. When the paste is mixed in the cylinder 4 and ready to dispense, the piston rod 7 and thereby the paddle 12 are pulled backwards until the ridges 23 engage with the grooves 24 (see FIG. 7). After establishment of this engagement, the safety pin 9 is removed (pulled out upwards in FIG. 6) and the paddle-piston assembly 12-13 is rotated as a unit. This rotation is possible due to the engagement between the ridges 23 and the grooves 24. After about 30-40 degrees rotation, a spring-loaded jamming mechanism 25 within the piston 13 is activated such that the paddle 12 and the piston 13 are connected and also displaceable within the cylinder 4 as a unit for dispensing the paste.

As is best seen in FIG. 9, the piston 13 has several elongate grooves 24 arranged in the shape of a star in the front surface of the piston 13. The paddle 12 has four arms each of which has an elongate ridge 23 for engagement with a groove 24.

By avoidance of the external ring of the prior-art device and by introduction of the inventive coupling mechanism and the inventive friction-reducing locking member assembly, several advantages are achieved and an improved device for mixing and dispensing paste has been accomplished. The releasable safety pin 9 with its dual function to allow both rotation and—by means of the jamming mechanism 25—also axial displacement of the paddle-piston assembly 12-13, makes it possible to achieve a very effective function of the device.

Finally it should be emphasised that the invention is not limited to the embodiments described herein, and modifications are feasible within the scope of the invention as it is defined in the appended claims. For instance, the number of covered locking members can vary and also the materials chosen.

The invention claimed is:

1. A single-use device for mixing paste ingredients, and for dispensing and applying a mixed paste, such as bone cement, comprising:
a cylinder for receiving the paste;
a piston which is arranged displaceable in the cylinder;
a piston rod which is displaceable and rotatable in the piston and which has an element for mixing the paste ingredients in the cylinder;
locking means configured to lock the piston rod in any position along the piston rod;
and means configured to interconnect the piston and the piston rod to allow displacement of the piston in the cylinder by means of the piston rod for dispensing of the mixed paste outside the cylinder;
said locking means comprising at least one locking member which has an aperture for receiving the piston rod displaceable therein;
wherein said locking member comprises a locking plate element having an aperture and an elastic material having an aperture the inner edge of which is at least partially in contact with the piston rod, said elastic material being configured to prevent contact between the piston rod and the inner edge of the locking plate element aperture.

2. The device as claimed in claim 1, wherein said elastic material comprises a cover element having an aperture coaxial with the aperture of the locking plate element and at least one projection in contact with the piston rod.

3. The device as claimed in claim 2, wherein the aperture of the cover element comprises a number of angularly spaced and opposed projections which are in contact with the piston rod.

4. The device as claimed in claim 1, comprising a pair of similar locking members comprising a cover element of said elastic material configured to prevent said contact between the rod and the inner edge of the locking plate element aperture.

5. The device as claimed in claim 1, wherein said elastic material is plastic.

6. The device as claimed in claim 2, wherein the locking plate element is of metal.

7. The device as claimed in claim 1, comprising a releasable latching member which in a mixing mode of the device prevents both rotation and displacement of the piston, and which in a dispensing mode of the device is removed for allowing rotation and displacement of a piston-mixing member assembly within the cylinder, wherein the piston-mixing member assembly is formed by interconnecting the piston with the piston rod and the mixing member.

8. A single-use device for mixing paste ingredients, and for dispensing and applying a mixed paste, such as bone cement, comprising:
a cylinder for receiving the paste;
a piston which is arranged displaceable in the cylinder;
a piston rod which is displaceable and rotatable in the piston and which has a mixing element for mixing the paste ingredients in the cylinder;
locking means configured to lock the piston rod in any position along the piston rod;
and means configured to interconnect the piston and the piston rod to allow displacement of the piston in the cylinder by means of the piston rod for dispensing of the mixed paste outside the cylinder;
wherein said mixing element comprises first coupling means configured to engage with matching second coupling means on the piston, so that the mixing element and the piston are rotatable together when engaged for establishing said interconnection of the piston and the piston rod;
wherein the mixing element is disposed at the end of the piston rod within the cylinder, said first coupling means comprising projections directed to the piston and said second coupling means comprising matching recesses which are formed in the piston and which are configured to receive said projections;
wherein said projections are elongate ridges disposed about the piston rod and said recesses are elongate grooves disposed about the piston rod in the piston; and
wherein the device comprises a retaining mechanism disposed within the piston that prevents axial movement of the piston and that is released when the engaged mixing element and piston are rotated at least a partial turn.

9. A single-use device for mixing paste ingredients, and for dispensing and applying a mixed paste, such as bone cement, comprising:
a cylinder for receiving the paste;
a piston which is arranged displaceable in the cylinder;
a piston rod which is displaceable and rotatable in the piston and which has a mixing element for mixing the paste ingredients in the cylinder;
locking means configured to lock the piston rod in any position along the piston rod, said locking means comprising at least one locking member which has an aperture for receiving the piston rod displaceable therein, wherein said locking member comprises a locking plate element having an aperture and an elastic material having an aperture the inner edge of which is at least partially in contact with the piston rod, said elastic material being configured to prevent contact between the piston rod and the inner edge of the locking plate element aperture;

a coupling structure for coupling the piston with the mixing element and piston rod to allow displacement of the piston in the cylinder by means of the piston rod for dispensing of the mixed paste outside the cylinder, the coupling structure comprising a plurality of elongate ridges and a plurality of elongate grooves, wherein the plurality of elongated grooves are constructed to receive the plurality of elongate ridges when the mixing element slides axially relative to the piston; and a releasable latching member which in a mixing mode of the device prevents both rotation and displacement of the piston, and which in a dispensing mode of the device is removed for allowing rotation and displacement of the piston-mixing member assembly within the cylinder.

10. The device of claim 9, wherein the mixing element comprises the plurality of elongated ridges and the piston comprises the plurality of elongated grooves.

* * * * *